(12) United States Patent
Nogami et al.

(10) Patent No.: US 9,678,031 B2
(45) Date of Patent: Jun. 13, 2017

(54) BIOCHIP AND BIODEVICE USING SAME

(71) Applicant: PANASONIC CORPORATION, Osaka (JP)

(72) Inventors: Takahiro Nogami, Osaka (JP); Takeki Yamamoto, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 246 days.

(21) Appl. No.: 14/375,106

(22) PCT Filed: Mar. 13, 2013

(86) PCT No.: PCT/JP2013/001635
§ 371 (c)(1),
(2) Date: Jul. 28, 2014

(87) PCT Pub. No.: WO2013/140748
PCT Pub. Date: Sep. 26, 2013

(65) Prior Publication Data
US 2014/0367257 A1    Dec. 18, 2014

(30) Foreign Application Priority Data

Mar. 19, 2012    (JP) .................................. 2012-061452

(51) Int. Cl.
*G01N 1/40*    (2006.01)
*B01L 3/00*    (2006.01)
(Continued)

(52) U.S. Cl.
CPC ............ *G01N 27/28* (2013.01); *B01L 3/5023* (2013.01); *G01N 1/4005* (2013.01); *A61M 1/34* (2013.01);
(Continued)

(58) Field of Classification Search
CPC ..... B01L 2300/0609; B01L 2300/0681; B01L 2300/0845; G01N 2011/4005; G01N 2011/4016; G01N 27/28
See application file for complete search history.

(56) References Cited

U.S. PATENT DOCUMENTS 4,167,482 A * 9/1979 Muller ................... B01D 35/10
                                                           210/411
4,701,267 A   10/1987 Watanabe et al.
(Continued)

FOREIGN PATENT DOCUMENTS

JP    60-203267 A    10/1985
JP    2005-148048 A    6/2005
(Continued)

OTHER PUBLICATIONS

International Search Report issued in International Application No. PCT/JP2013/001635 with the mailing date of May 14, 2013, with English Translation.

*Primary Examiner* — Louis Rufo
(74) *Attorney, Agent, or Firm* — McDermott Will & Emery LLP

(57) ABSTRACT

A biochip including a plate-like diaphragm part provided with a through-hole, a wall part provided at an outer periphery of the diaphragm part, and a reinforcing part formed in a portion other than the through-hole in the diaphragm part.

16 Claims, 15 Drawing Sheets

(51) Int. Cl.
*G01N 33/49* (2006.01)
*A61M 1/34* (2006.01)
*G01N 27/28* (2006.01)

(52) U.S. Cl.
CPC . *A61M 2202/0429* (2013.01); *A61M 2205/75* (2013.01); *B01L 2200/12* (2013.01); *B01L 2300/0609* (2013.01); *B01L 2300/0636* (2013.01); *B01L 2300/0681* (2013.01); *B01L 2300/0832* (2013.01); *G01N 33/491* (2013.01)

(56) References Cited

U.S. PATENT DOCUMENTS

2006/0252044 A1* 11/2006 Okumura ............ B01L 3/50255
  435/6.11
2010/0219488 A1*  9/2010 Nakatani ............. B81C 1/00206
  257/414
2011/0120864 A1   5/2011 Takahashi et al.

FOREIGN PATENT DOCUMENTS

| JP | 2010-213668 A | 9/2010 |
| WO | 2010/016193 A1 | 2/2010 |

* cited by examiner

BIOCHIP AND BIODEVICE USING SAME

RELATED APPLICATIONS

This is the national phase of International Application No. PCT/JP2013/001635, with an international filing date of Mar. 13, 2013, which claims priority of Japanese Patent Application No. 2012-061452, filed on Mar. 19, 2012, the contents of each of which are hereby incorporated by reference.

TECHNICAL FIELD

The present invention relates to a biochip used as a sensor chip or a filter chip and to a biodevice using the same. The sensor chip is used in a Micro-Total Analysis System, an Electrochemical Analysis Chip, a micro-reactor, Lab on a chip, a nanochip, a biochip, or the like, for electrical or physicochemical measurement of a cell. The biochip is used for extracting a solute from a solvent, fine particles, or the like, or for extracting or separating blood cells contained in a solution derived from a human or animal living body.

BACKGROUND ART

FIG. 25 is a sectional view of conventional biochip 12. Biochip 12 used as a cell electrophysiological sensor chip includes plate-like diaphragm part 13 and wall part 18. Diaphragm part 13 has first surface 14 and second surface 15 provided to a reverse side of first surface 14. Diaphragm part 13 is provided with through-hole 16 penetrating through first surface 14 and second surface 15. Wall part 18 is provided at the outer periphery of first surface 14 of diaphragm part 13.

For example, when a solution including a cell is allowed to flow from first surface 14 of diaphragm part 13, the cell is allowed to adhere and held on through-hole 16. Thereafter, by infusing a drug into through-hole 16, physicochemical stimulation is applied to the cell and an internal fluid of the cell is discharged to second surface 15. By measuring an electric potential change between first surface 14 and second surface 15, reaction of the cell to the physicochemical stimulation can be measured.

Note here that prior art literature relating to the invention of this application includes, for example, Patent Literature 1.

CITATION LIST

Patent Literature

PTL 1: Japanese Patent Unexamined Publication No. 2010-213668

SUMMARY OF THE INVENTION

A biochip of the present invention includes a plate-like diaphragm part provided with a through-hole, a wall part provided at the outer periphery of the diaphragm part, and a reinforcing part formed in a portion other than the through-hole in the diaphragm part.

DESCRIPTION OF EMBODIMENTS

In conventional biochip 12, diaphragm part 13 is provided with through-hole 16 by etching. However, it is difficult to form a through-hole having a large aspect ratio (a ratio of the depth to the width), and it is difficult to increase a thickness of diaphragm part 13. Therefore, it is difficult to enhance the strength of diaphragm part 13. As a result, diaphragm part 13 may be displaced or destroyed by suction to allow a cell to adhere, or adhesiveness of the cell may be weakened.

Furthermore, when biochip 12 is used as a filter chip, a filter medium made of a separation structure is further disposed on first surface 14. However, as increase in pressure loss due to accumulation of residues at the time of filtration, diaphragm part 13 may be damaged. On the other hand, when a thickness of diaphragm part 13 is increased in order to enhance the strength, the flow passage resistance of through-hole 16 is increased, and thus, through-hole 16 is easily clogged with a substance. Furthermore, when a thickness of diaphragm part 13 is reduced, a damage rate is increased. Furthermore, as a mesh of the filter medium made of a separation structure becomes finer, the filter property is higher but pressure loss is increased. Therefore, high pressure needs to be applied in order to carry out filtration for a short time, and diaphragm part 13 having high pressure resistance is required.

Hereinafter, exemplary embodiments of the present invention are described with reference to drawings. Note here that the present invention is not necessarily limited to the following exemplary embodiments.

(First Exemplary Embodiment)

Firstly, as a biodevice using a biochip in accordance with a first exemplary embodiment, a cell electrophysiological sensor device using a cell electrophysiological sensor chip is described as an example.

Figure 1:
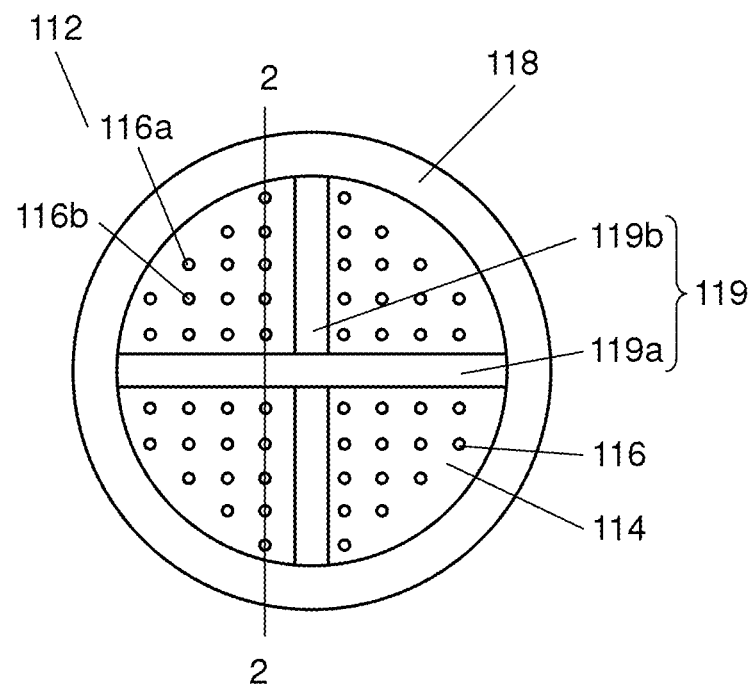
FIG. 1 is a top view of a biochip in accordance with a first exemplary embodiment of the present invention.
Figure 2:
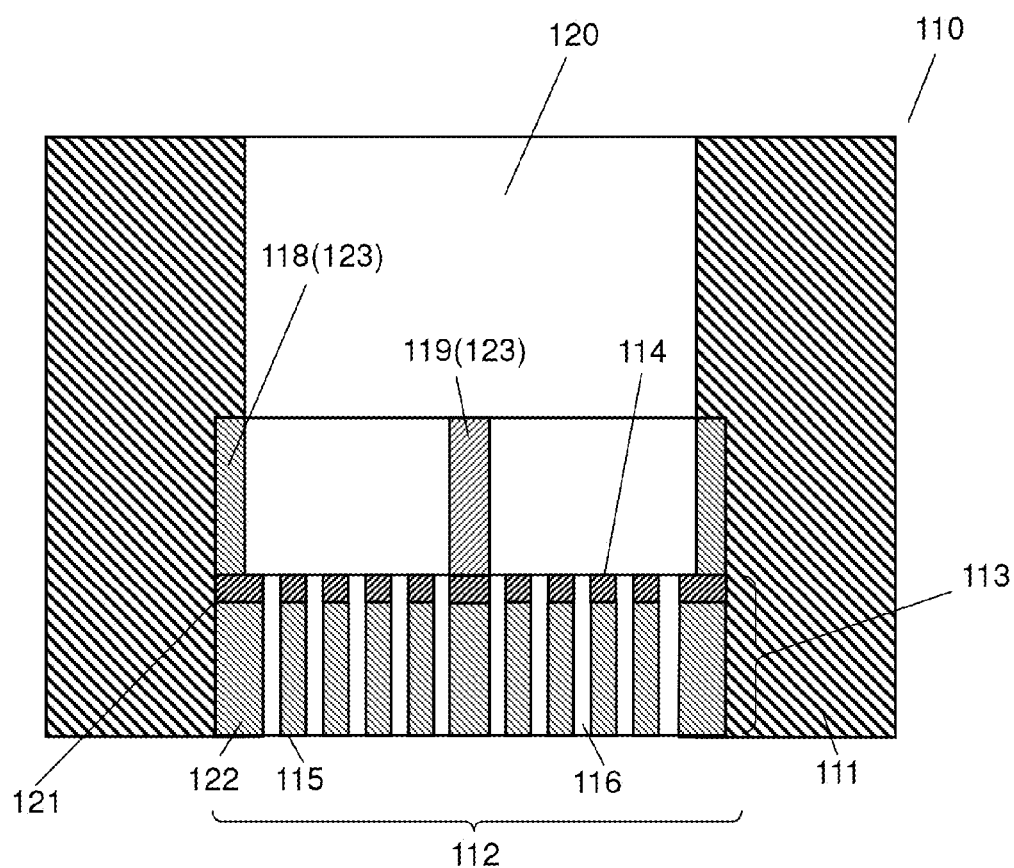
FIG. 2 is a sectional view of a biodevice in accordance with the first exemplary embodiment of the present invention.

FIG. 1 is a top view of a biochip in accordance with the first exemplary embodiment. FIG. 2 is a sectional view of a biodevice using the biochip shown in FIG. 1. FIG. 2 corresponds to a sectional view taken on line 2-2 of FIG. 1.

Biochip 112 includes plate-like diaphragm part 113 provided with through-hole 116 (first through-hole), wall part 118 provided at the outer periphery of diaphragm part 113, and reinforcing part 119 formed in a portion other than through-hole 116 in diaphragm part 113.

Diaphragm part 113 includes first surface 114 and second surface 115. Through-hole 116 penetrates through first surface 114 and second surface 115.

It is desirable that diaphragm part 113 is formed of, for example, a thin plate and that the reverse side of first surface 114 is second surface 115.

Through-hole 116 may be formed in at least one portion of diaphragm part 113. However, in order to measure a larger amount of cells at one time, it is desirable that a plurality of through-holes 116 is formed.

Annular wall part 118 is provided at the outer periphery of diaphragm part 113. When annular wall part 118 is provided at the outer periphery of diaphragm part 113 in such a manner that it is integrated with diaphragm part 113, biodevice 110 can be easily held when diaphragm part 113 is handled or mounted. In particular, when diaphragm part 113 is a thin plate, wall part 118 is useful. Herein, the annular shape includes circular and elliptic shapes, and polygonal shapes such as a triangular shape and a quadrangular shape seen in the top view. The annular shape includes any other shapes as long as they seamlessly surround the outer periphery of diaphragm part 113 by suitable shapes for the shape of diaphragm part 113. That is to say, the shape in the top view of diaphragm part 113 or biochip 112 may be various shapes including a circular shape or a polygonal shape. When biochips 112 are produced from a silicon wafer, a square shape or a rectangular shape is preferable because the shapes can be arranged densely, thus increasing the number of products.

Reinforcing part 119 is provided to a portion excluding through-hole 116 on first surface 114 of diaphragm part 113 such that reinforcing part 119 is connected to diaphragm part 113.

Reinforcing part 119 has, for example, a plate-like shape, and is formed perpendicular to a surface (first surface 114) of diaphragm part 113. It is desirable that reinforcing part 119 is connected to not only diaphragm part 113 excluding a part provided with wall part 118 but also the inner side surface of wall part 118. With this structure, pressure (force) to diaphragm part 113 can be dispersed, and diaphragm part 113 can be prevented from being damaged.

For example, as shown in FIG. 1, reinforcing part 119 is connected to first surface 114 of diaphragm part 113 by direct bonding, and also connected to the inner side surface of wall part 118 by direct bonding. Herein, the direct bonding denotes bonding without using additional members such as an adhesive agent, and also includes unitarily forming.

At least one reinforcing part 119 may be formed on a part excluding wall part 118 on diaphragm part 113, and two or more reinforcing parts 119 may be formed. When a plurality of reinforcing parts 119 is formed, pressure resistance with respect to force applied perpendicular to diaphragm part 113 can be improved. Furthermore, for example, as shown in FIG. 1, first reinforcing part 119a and second reinforcing part 119b may be formed such that they cross each other.

It is preferable that first reinforcing part 119a and second reinforcing part 119b cross each other at right angles such that force to diaphragm part 113 can be uniformly dispersed. Furthermore, it is preferable that first reinforcing part 119a and second reinforcing part 119b are connected to first surface 114 and wall part 118.

Note here that the forms of first reinforcing part 119a and second reinforcing part 119b are not necessarily limited to a form in which they cross each other at right angles. They may take forms such as a form including only reinforcing part 119a, a curved form (not shown), or a form in which a plurality of curved forms crosses each other. Furthermore, in order to relieve flow passage resistance, it is preferable that a tip (upper surface) of reinforcing part 119 has an acuminate shape or a forward tapered shape. Furthermore, the height of reinforcing part 119 and the height of wall part 118 may be different from each other.

Reinforcing part 119 is formed in a position other than the opening part of through-hole 116 on diaphragm part 113 so as not to hinder the close adhesion and holding of a cell to the opening part of through-hole 116.

It is desirable that a thickness of reinforcing part 119 is as large as possible in a range of a space between the most adjacent two through-holes 116. Herein, "the most adjacent two through-holes 116" denote through-holes 116 in relation that a distance between a center of through-hole 116a and a center of through-hole 116b is the most adjacent.

Note here that the shape of reinforcing part 119 may be a columnar or tubular shape instead of a plate-like shape.

However, when reinforcing part 119 has a plate-like shape and is connected to the inner surface of wall part 118, the strength of diaphragm part 113 can be further improved. Therefore, diaphragm part 113 having weak strength can be prevented from being damaged.

As shown in FIG. 2, biodevice 110 includes mount base 111 having hole 120 (second through-hole) and biochip 112 provided to one end of hole 120. A solution flowing in hole 120 is brought into contact with biochip 112.

Biochip 112 has, for example, a circular shape, and is fitted into mount base 111 having circular hole 120.

When biochip 112 is bonded to the inside of a capillary, it can be used as a patch pipette type biodevice. Furthermore, when biochip 112 is mounted on a substrate made of glass, resin, or the like, it can be used as an array type biodevice.

Mount base 111 is made of material such as glass and resin. Mount base 111 is formed of glass such as quartz glass, borosilicate glass, soda-lime glass, potash glass, crystal glass, uranium glass, and acrylic glass. Alternatively, mount base 111 may be resin such as polypropylene, polyurethane, polyvinyl chloride, polyvinyl acetate, polytetrafluoroethylene, acrylonitrile butadiene styrene, polyacetal, polybutylene terephthalate, polyolefin, polystyrene, polydimethyl siloxane, polyamide, polycarbonate, polyethylene terephthalate, polyphenylene sulfide, polyether ether ketone, and polymethylmethacrylate. Alternatively, mount base 111 may be composite material of the above-mentioned resin and glass. Alternatively, mount base 111 may be rubber such as silicone rubber, acrylic rubber, nitrile rubber, isoprene rubber, urethane rubber, ethylene propylene rubber, chlorosulfonated polyethylene, epichlorohydrin rubber, chloroprene rubber, butadiene rubber, fluororubber, and polyisobutylene. Alternatively, mount base 111 may be composite material of the above-mentioned rubber and glass.

Biochip 112 only needs to be bonded to the inside of hole 120 of mount base 111. Examples of the bonding method include directly bonding and bonding via an adhesive layer.

It is preferable that biochip 112 is produced by using a SOI (Silicon On Insulator) substrate, as base material, including a silicon layer made of silicon (100) by a manufacturing method mentioned below. The SOI substrate has a three-layered structure of silicon layer 122—silicon dioxide layer 121—silicon layer 123. This SOI substrate is microprocessed by photo lithography and etching technology, thus enabling a large number of biochips 112 to be produced at one time.

When the SOI substrate is subjected to etching process, silicon dioxide layer 121 plays a role of an etching stop layer. Furthermore, since silicon dioxide layer 121 is rich in hydrophilicity, it becomes easy to suppress generation of air bubbles and to remove air bubbles at the time of measurement. Thus, highly precise measurement can be carried out.

A thickness of silicon dioxide layer 121 is preferably 0.5 nm or more and 10 nm or less from the viewpoint of a thickness required as the etching stop layer and productivity.

Silicon dioxide layer 121 which functions as the etching stop layer is generally a silicon dioxide layer formed by thermal oxidation. However, silicon dioxide layer 121 may be a silicon dioxide layer formed by other methods such as a CVD (Chemical Vapor Deposition) method, a sputtering method, and a CSD (Chemical Solution Deposition) method. Furthermore, silicon dioxide layer 121 may be a doped oxide layer such as a PSG (Phosphorus Silicon Glass) layer doped with phosphorous, or a BPSG (Boron Phosphorus Silicon Glass) layer doped with phosphorous and boron. Furthermore, not only a layer including silicon dioxide as a main component mentioned above but also layers of inorganic oxides or inorganic nitrides such as silicon nitride, silicon oxynitride, and aluminum oxide, which have a difference in etching rates with respect to silicon, may be used instead of silicon dioxide layer 121.

Herein, the SOI substrate including silicon (100) is used as the base material for producing biochip 112, but a silicon (110) substrate, a silicon (111) substrate, and silicon substrates having other plane orientations may be used. Since the use of an amorphous silicon substrate suppresses easily splitting of diaphragm part 113 along the plane orientation, a silicon substrate which does not have a plane orientation may be used. Furthermore, other substrates such as a glass substrate and film resin besides silicon substrates may be used.

From the viewpoint of workability and versatility, however, it is preferable to use a substrate including silicon (100) as the base material for producing biochip 112. The substrate including silicon (100) only needs to include at least silicon (100).

Furthermore, by changing the number of mask holes of a resist mask when through-holes 116 are produced, the number of through-holes 116 can be changed.

When the number of through-holes 116 is increased, a large number of cells can be measured at one time. Therefore, a large number of cells can be measured for a short time without increasing an area of biochip 112, and working efficiency is improved. Furthermore, a plurality of through-holes 116 in first surface 114 of diaphragm part 113 is preferably arranged in a honeycomb shape. By arranging through-holes 116 in a honeycomb shape, a larger number of through-holes 116 per unit area can be formed without reducing the strength of diaphragm part 113.

Furthermore, when a film of silicon dioxide is added to a silicon surface of reinforcing part 119 by thermal oxidation, hydrophilicity can be improved. As a result, it becomes easy to suppress generation of air bubbles and to remove air bubbles at the time of measurement. Thus, highly precise measurement can be carried out.

In order to facilitate removal of air bubbles when a solution is infused into biochip 112, the surface (at least a side surface) of reinforcing part 119 has preferably a wave shape or a sawtooth shape.

The surface of wall part 118 has preferably a wave shape or a sawtooth shape to facilitate removal of air bubbles. Wall part 118 and reinforcing part 119 may be formed of different material from each other, but they are preferably formed of the same material. It is desirable that diaphragm part 113, wall part 118 and reinforcing part 119 of biochip 112 are made of the same base material. For example, when the base material is silicon, the shape change or the like can be carried out by changing resist masks.

It is preferable that the surface of biochip 112 is made of material rich in hydrophilicity. When the surfaces of diaphragm part 113, wall part 118, and reinforcing part 119 are coated with a hydrophilic film (not shown), respectively, it becomes easy to suppress generation of air bubbles and to remove air bubbles at the time of measurement. Thus, highly precise measurement can be carried out.

Furthermore, the hydrophilic film can be formed of a silicon oxide film, an oxynitride film, or the like. That is to say, coating with the hydrophilic film can be carried out by subjecting the silicon surface of wall part 118 and reinforcing part 119 to thermal oxidation or thermal nitriding. At this time, by coating wall part 118 and reinforcing part 119 at the same time, coating can be carried out efficiently, thus enhancing the productivity.

Figure 19:
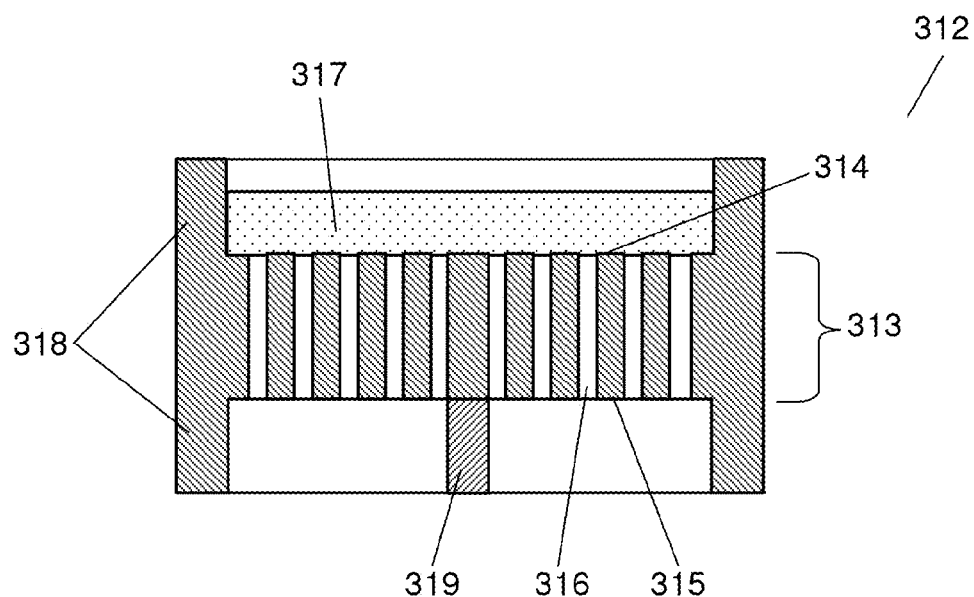
FIG. 19 is an enlarged sectional view of a principal part of a biochip in accordance with a third exemplary embodiment of the present invention.

In FIG. 2, reinforcing part 119 is connected to first surface 114 of diaphragm part 113. However, reinforcing part 119 simply needs to be connected to a surface of diaphragm part 113. As shown in FIG. 19 mentioned later, reinforcing part 119 may be connected only to second surface 115 without being connected to first surface 114. In this case, since reinforcing part 119 is not formed on first surface 114, when a cell is allowed to adhere and held by the opening part of through-hole 116 formed in first surface 114 without being hindered.

Figure 22:
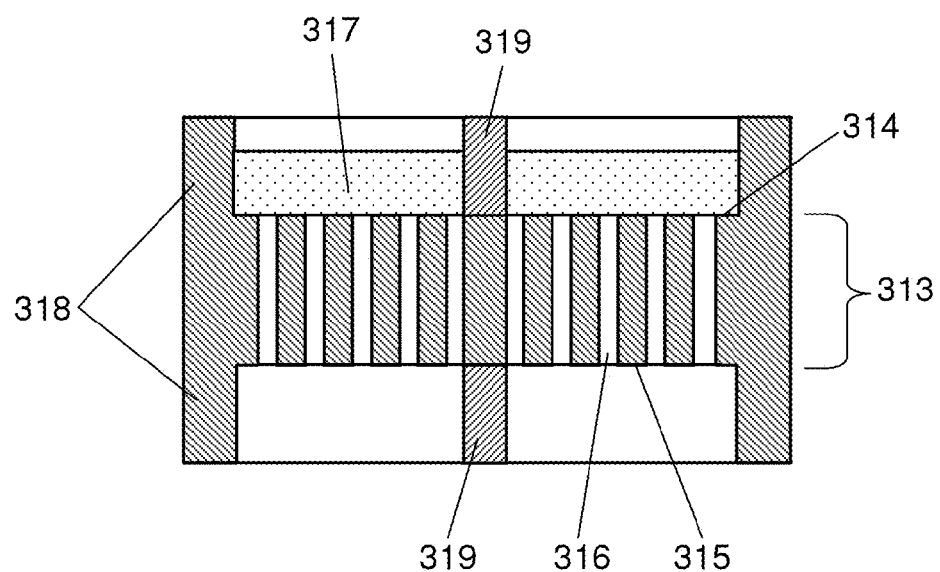
FIG. 22 is an enlarged sectional view of a principal part of a biochip in accordance with the third exemplary embodiment of the present invention.

Alternatively, as shown in FIG. 22 mentioned later, reinforcing part 119 may be formed on both surfaces of diaphragm part 113 (that is to say, first surface 114 and second surface 115). When reinforcing part 119 is formed on both surfaces of diaphragm part 113, diaphragm part 113 becomes stronger.

Note here that wall part 118 may be also formed on first surface 114 and/or second surface 115 of diaphragm part 113 depending upon the formation position of reinforcing part 119.

It is desirable that material of first surface 114 of diaphragm part 113 includes silicon (100), and reinforcing part 119 is formed in the vertical direction with respect to silicon (110) plane as a cleavage plane. That is to say, the 2-2 direction shown in FIG. 1 or a direction orthogonal to this direction is a cleavage plane, and reinforcing part 119 is formed in the vertical direction with respect to the cleavage plane.

The cleavage plane is a plane whose mechanical strength to stress from a specific direction is lower than the mechanical strength from other directions.

Unlike film resin which is easily deformed and free from a problem of splitting, silicon single crystal material may be brittle and easily broken, or diaphragm part 113 may easily split due to its cleavage property. In particular, the cleavage is destruction occurring in a plane having a weak interatomic binding force in a crystal structure, so that the cleavage easily occurs due to flaw, crack, or the like, in the substrate during production process.

Furthermore, since displacement corresponding to stress is maximum in the longest line segment of diaphragm part 113 (that is to say, in the diagonal line direction of an auxiliary wall), this part is most likely to split. At this time, assuming that reinforcing part 119 is formed on the diagonal line of the cleavage plane, the longest line segment of diaphragm part 113 coincide with the cleavage plane, so that diaphragm part 113 easily splits.

However, when reinforcing part 119 is formed in the vertical direction with respect to the cleavage plane, the longest line segment of diaphragm part 113 is not along the cleavage plane, so that splitting can be reduced.

Also in a case where base material other than silicon (100) is used, similarly, reinforcing part 119 only needs to be disposed such that the longest line segment of diaphragm part 113 does not coincide with the cleavage plane.

It is desirable that a line segment linking the centers of nearest neighbor through-holes 116 is disposed so as not to be parallel to the cleavage plane of silicon. The line segment linking the centers of nearest neighbor through-holes 116 is a structurally brittle part. When this line segment coincides with the cleavage plane, diaphragm part 113 easily splits. That is to say, when the line segment linking the centers of nearest neighbor through-holes 116 is disposed not to be parallel to the cleavage plane of silicon, diaphragm part 113 does not easily split.

Also in a case where base material other than silicon (100) is used, similarly, the line segment linking the centers of nearest neighbor through-holes 116 is disposed not to be parallel to the cleavage plane of silicon.

Next, a method for manufacturing biochip 112 is described.

Figure 3:
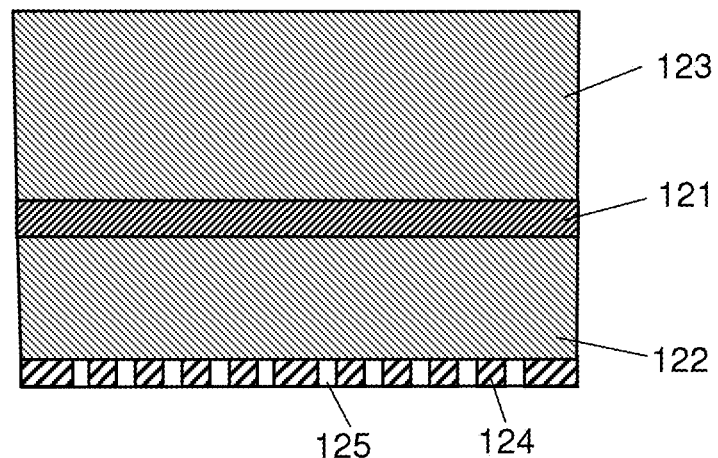
FIG. 3 is a sectional view showing a manufacturing step of the biochip in accordance with the first exemplary embodiment of the present invention.

Firstly, as base material for producing biochip 112, as shown in FIG. 3, a SOI substrate is prepared. The SOI substrate has a three-layered structure of silicon layer 122—silicon dioxide layer 121—silicon layer 123 in which silicon layer 122 includes silicon (100).

Then, first resist mask 124 is formed on a surface (lower surface in FIG. 3) of silicon layer 122. At this time, a plurality of mask holes 125 having substantially the same shape as the shapes of the cross-sections of a plurality of desired through-holes is patterned for each biochip.

Figure 4:
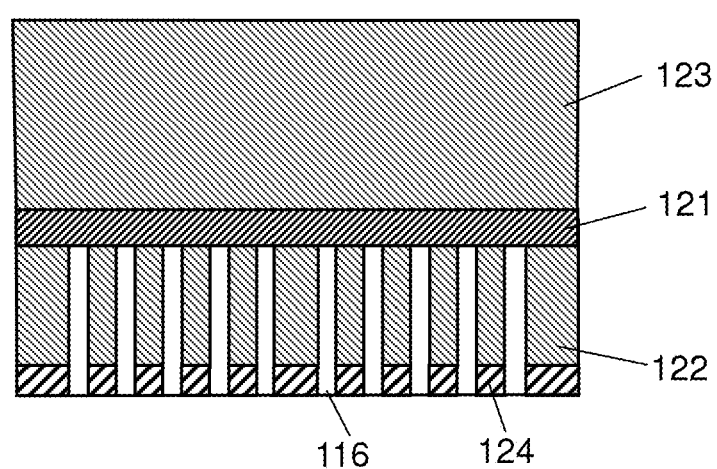
FIG. 4 is a sectional view showing a manufacturing step of the biochip in accordance with the first exemplary embodiment of the present invention.

Next, as shown in FIG. 4, silicon layer 122 is etched from a mask hole 125 side to form through-hole 116. As the etching method at this time, dry etching is desirable because highly precise micromachining can be carried out. When dry etching is carried out, in order to form through-hole 116 having a large aspect ratio, that is to say, through-hole 116 which is deep with respect to the hole diameter, a gas for promoting etching (etching gas) and a gas for suppressing etching (suppressing gas) are alternately used. In this exemplary embodiment, $SF_6$ is used as the etching gas and $C_4F_8$ is used as the suppressing gas. Ion collision of the etching gas allows etching to proceed in the physically vertical direction in silicon layer 122. Next, $CF^+$ contained in the suppressing gas is attached to the wall surface of the dry etching hole of silicon layer 122 without being biased, so that a uniform polymer film made of fluorocarbon is formed on the surface. When such etching is carried out repeatedly, then the etching reaches the surface of silicon dioxide layer 121, and entering of the etching in the depth direction stops at the surface of silicon dioxide layer 121.

Figure 5:
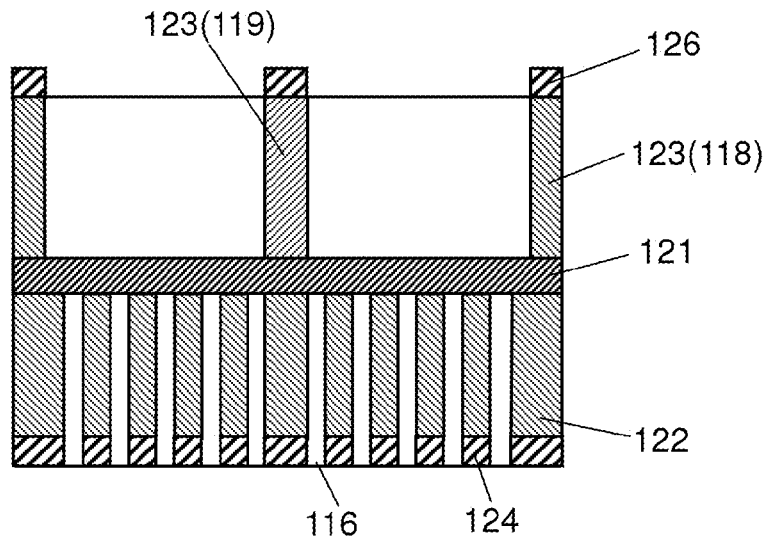
FIG. 5 is a sectional view showing a manufacturing step of the biochip in accordance with the first exemplary embodiment of the present invention.

Next, as shown in FIG. 5, second resist mask 126 is formed on a surface (upper surface in FIG. 5) of silicon layer 123. Then, silicon layer 123 is etched in the same etching conditions as those when silicon layer 122 is etched. Thus, wall part 118 and reinforcing part 119 are formed. The proceeding of this etching in the depth direction also stops at the surface of silicon dioxide layer 121.

Figure 6:
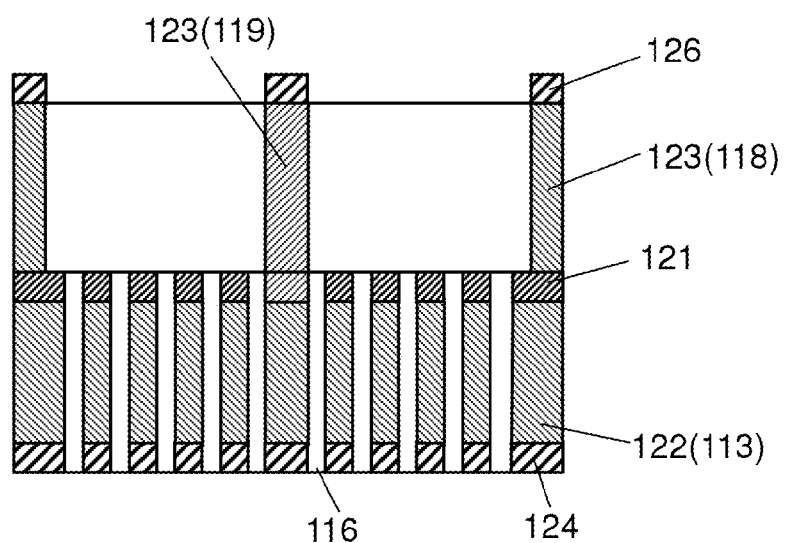
FIG. 6 is a sectional view showing a manufacturing step of the biochip in accordance with the first exemplary embodiment of the present invention.

Next, as shown in FIG. 6, silicon dioxide layer 121 is etched from a surface of silicon layer 122 (lower surface in FIG. 6). As the etching gas to be used for this dry etching, for example, a mixture gas of $CHF_3$ and Ar is used. In the mixture gas of $CHF_3$ and Ar, a plasma-excited Ar gas serves as an etching gas having high straightness. When a large amount of a component, for example, an Ar ion, for carrying out sputtering, is used, the etching proceeds straight to the inside of through-hole 116, and only silicon dioxide layer 121 can be etched.

Other etching gases to be used at this time include $CF_4$, He, and $SF_6$.

Thereafter, first resist mask 124 and second resist mask 126 are washed and peeled off, so that biochip 112 is subjected to thermal oxidation or thermal nitriding, the entire surface of biochip 112 is coated with a hydrophilic film (not shown).

(Second Exemplary Embodiment)

Hereinafter, as a biodevice using a biochip in accordance with a second exemplary embodiment, a filter device using a filter chip is described as an example with reference to drawings.

Figure 7:
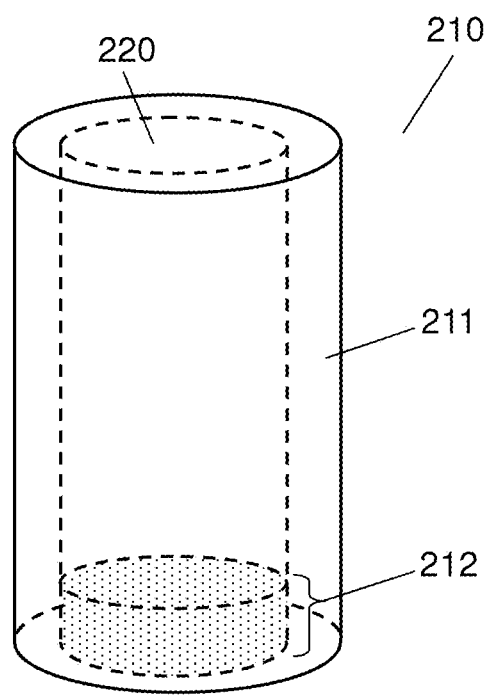
FIG. 7 is a perspective view of a biodevice in accordance with a second exemplary embodiment of the present invention.
Figure 8:
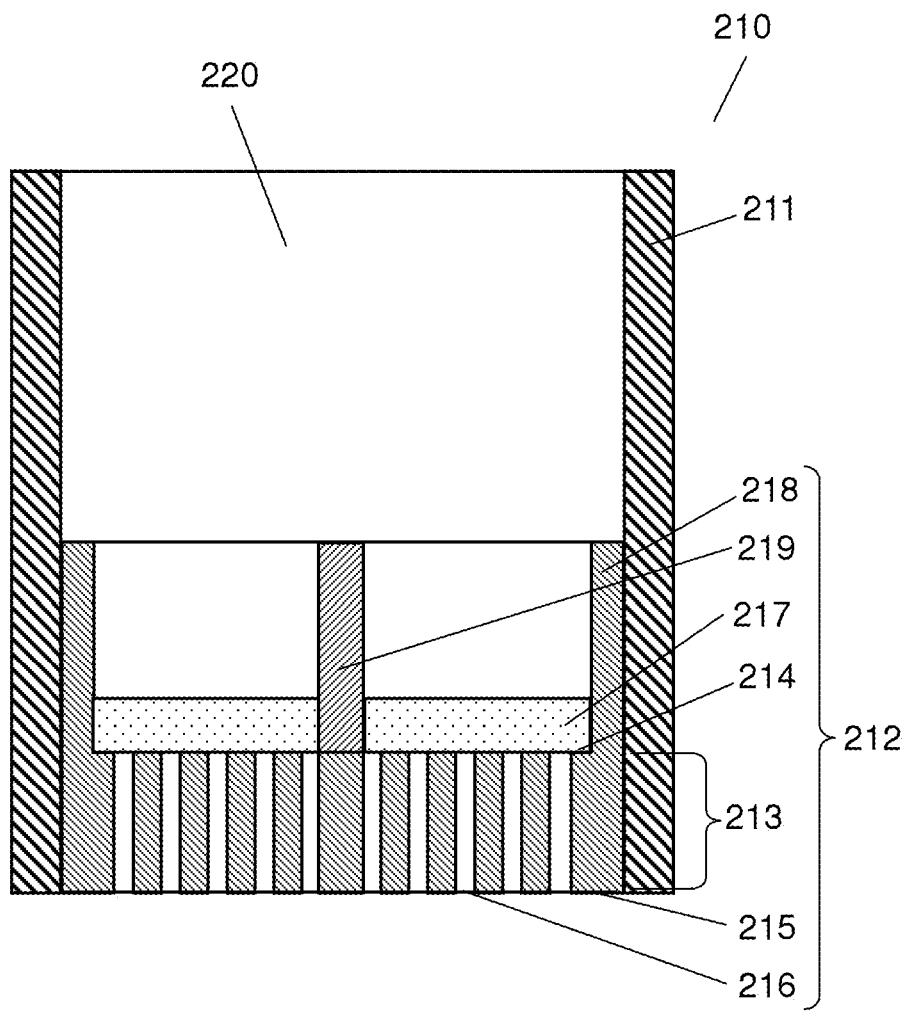
FIG. 8 is a sectional view of the biodevice in accordance with the second exemplary embodiment of the present invention.
Figure 9:
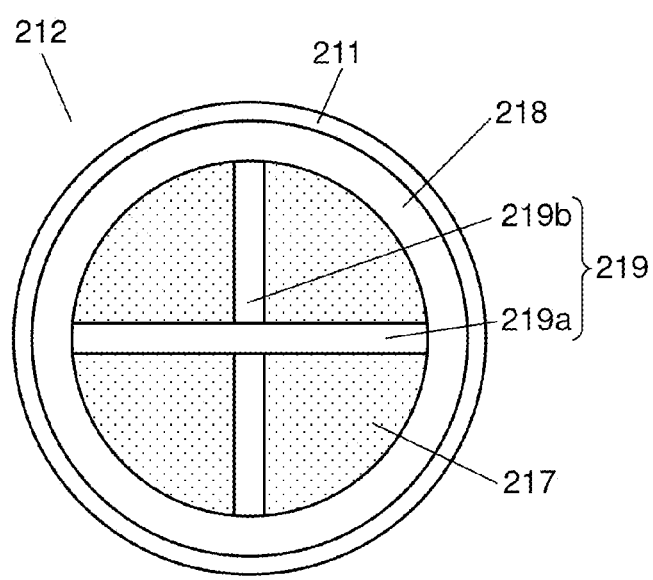
FIG. 9 is a top view of a biochip in accordance with the second exemplary embodiment of the present invention.

FIG. 7 is a perspective view of a biodevice in accordance with the second exemplary embodiment. FIG. 8 is a sectional view of the biodevice in accordance with the second exemplary embodiment. FIG. 9 is a top view of a biochip in accordance with the second exemplary embodiment. Biodevice 210 includes mount base 211 having hole 220, and biochip 212 provided at the inside of hole 220. A solution flowing in hole 220 is brought into contact with biochip 212.

Biochip 212 includes plate-like diaphragm part 213. Diaphragm part 213 is provided with through-hole 216 penetrating through first surface 214 and second surface 215 facing first surface 214. Annular wall part 218 for holding diaphragm part 213 is formed on outer periphery of first surface 214 of diaphragm part 213. Fibrous substance 217 is disposed so as to coat the upper side of first surface 214 and an opening part of through-hole 216. Reinforcing part 219 is provided to a portion which is not coated with fibrous substance 217. Reinforcing part 219 is connected to diaphragm part 213.

For example, as shown in FIG. 8, diaphragm part 213 is provided with a plurality of through-holes 216. As shown in FIG. 9, fibrous substance 217 directly bonded from first surface 214 of diaphragm part 213 is provided in a portion in which first reinforcing part 219a and second reinforcing part 219b are not formed on first surface 214 of diaphragm part 213.

Fibrous substance 217 is formed of a plurality of fibrous substances 217, which are made of, for example, amorphous silicon oxide, entangled with each other.

For example, a solution is infused from the upper side of biochip 212. Among material contained in the solution, material whose maximum diameter is larger than the gap in fibrous substance 217 is captured as a filtration residue by fibrous substance 217. Material whose maximum diameter is smaller than the gap in fibrous substance 217 passes, as filtrate, through fibrous substance 217. Thus, the filtration residue and other material in the solution can be separated from each other. However, even when material has a maximum diameter larger than the gap in fibrous substance 217, the material may be able to be extracted as filtrate when the material can be deformed easily. Even when the material is larger than through-hole 216, the material may be able to pass through through-hole 216 by using the deformability when the material passes through through-hole 216. Note here that when the diameter of the filtration residue contained in the solution is smaller than the diameter of through-hole 216, the solution may be infused from the lower side of biochip 212, that is, through-hole 216.

As the base material for producing biochip 212, similar to the first exemplary embodiment, it is preferable to use a SOI (Silicon On Insulator) substrate including a silicon layer made of silicon (100). As the base material for producing biochip 212, a silicon (110) substrate, a silicon (111) substrate or other silicon substrates having the plane orientation in addition to silicon (100) may be used. Furthermore, use of an amorphous silicon substrate suppresses easily splitting of diaphragm part 213, which is most subject to force at the time of filtration, along the plane orientation. Therefore, a silicon substrate, which does not have a plane orientation, may be used.

When a thickness of diaphragm part 213 is increased, diaphragm part 213, which is most subject to force at the time of filtration, does not easily split. However, when micro through-hole 216 is provided, it is difficult to form a through-hole having a large aspect ratio by etching such as Bosch process. Therefore, the thickness of diaphragm part 213 is desirably about 5 µm or more and 100 µm or less.

When an area of diaphragm part 213 is similarly increased, an area of fibrous substance 217 is similarly increased, so that the filtration efficiency is increased. However, when the area is increased, since a displacement amount of diaphragm part 213 is increased, the strength is reduced. Therefore, the area of diaphragm part 213 is desirably 1200 µm$^2$ or less.

Through-hole 216 only needs to be formed such that it penetrates through at least one portion of first surface 214 to second surface 215 of diaphragm part 213. By changing the number of mask holes of a resist mask when through-holes 216 are produced, the number of through-holes 216 can be changed.

It is preferable that the number of through-holes 116 is increased, because filtrate easily passes through through-holes 116, the same amount of solution can be filtrated for a short time without increasing the area or a filtration pressure of biochip 212, and the working efficiency of a filter is improved. It is preferable that a plurality of through-holes 216 in first surface 214 of diaphragm part 213 is arranged in a honeycomb shape as in the first exemplary embodiment. Thus, a larger amount of through-holes 216 can be formed per unit area without deteriorating the strength of diaphragm part 213.

Note here that a diameter of through-hole 216 can be adjusted to a diameter suitable for suppressing occurrence of the flow passage resistance of the solution. For example, when a solution derived from a living body and including blood or erythrocyte is used as a solution, and erythrocyte is extracted as a filtrated substance, the diameter of through-hole 216 is preferably 3 µm or more.

Figure 10:
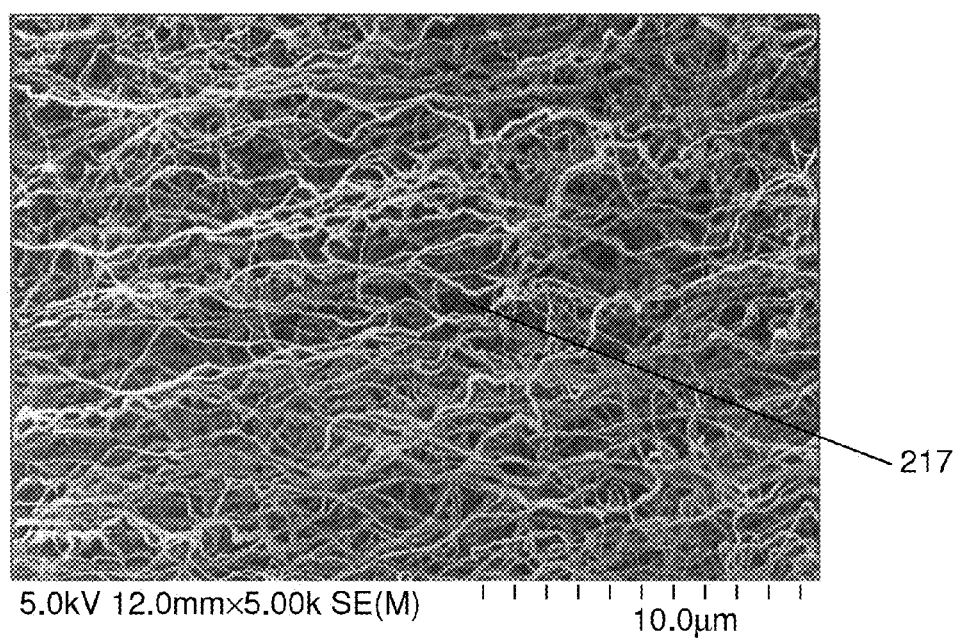
FIG. 10 is a SEM (Scanning Electron Microscope) photograph showing a fibrous substance of the biochip in accordance with the second exemplary embodiment of the present invention.

FIG. 10 is a SEM (Scanning Electron Microscope) photograph of fibrous substance 217 of biochip 212 in accordance with the second exemplary embodiment. Fibrous substance 217 is formed of, for example, oxide of silicon, which includes silicon oxide as a main component, and is preferably formed of amorphous silicon dioxide. A fiber thickness of fibrous substance 217 is about 0.01 µm or more and 2.0 µm or less. Fibrous substance 217 is directly bonded to diaphragm part 213, in which fibers of fibrous substances 217 are formed such that they are densely entangled with each other and some fibers branch into various directions. Herein, "directly bonded" denotes a state in which fibrous substance 217 is directly formed on diaphragm part 213, and diaphragm part 213 and atoms or molecules constituting fibrous substance 217 are directly bound to each other. In general, it denotes a state in which molecules are firmly bound to each other to form a covalent linkage.

Since fibers of fibrous substance 217, which are directly bound to diaphragm part 213, are entangled with each other and branch into a plurality of fibers, fibrous substance 217 is firmly formed to first surface 214 of diaphragm part 213. Furthermore, since the fibers of fibrous substance 217 are entangled with each other in a state in which each of the fibers bends, they are formed without spaces from various directions including the upper side of the opening part of through-hole 216 of first surface 214. Note here that the fiber thicknesses of the fibers of fibrous substance 217 may not be uniform, and fibers having various fiber thicknesses may be contained.

The shortest length of a space between fibers of fibrous substance 217 should be smaller than a size of the filtration residue. For example, when blood is used as a solution, leukocyte is obtained as the filtration residue and erythrocyte is extracted as a filtered product, the gap between fibers of fibrous substance 217 is desirably 1 µm or more and 6 µm or less. When the gap in fibrous substance 217 is 1 µm or more and 6 µm or less, only erythrocyte can be allowed to pass through the gap.

For fibrous substance 217, amorphous silicon dioxide is more desirably used as compared with single crystal silicon dioxide, because amorphous silicon dioxide is not easily broken.

Figure 11:
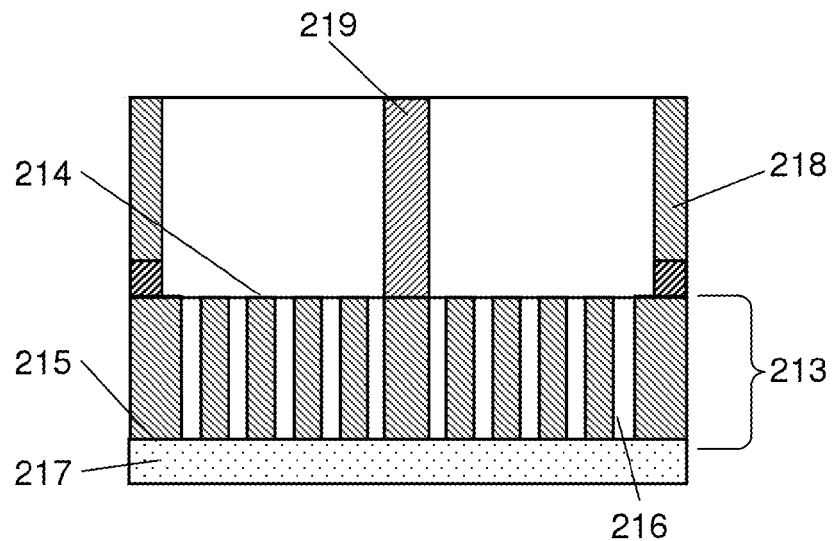
FIG. 11 is an enlarged sectional view of a principal part of the biochip in accordance with the second exemplary embodiment of the present invention.

Note here that in FIG. 8, fibrous substance 217 is formed so as to cover the opening part of through-hole 216 and to coat first surface 214. However, as shown in FIG. 11, fibrous substance 217 may be formed so as to cover the opening part of through-hole 216 and to coat the upper side of second surface 215. That is to say, fibrous substance 217 may be provided to at least any one of first surface 214 or second surface 215. When fibrous substance 217 is formed as shown in FIG. 11, since reinforcing part 219 and fibrous substance 217 are formed separately from each other, fibrous substance 217 can be formed on the whole part of second surface 215 of diaphragm part 213. Therefore, a capturing region is increased and capturing performance is improved.

Next, a method for manufacturing biochip 212 is described. Herein, a manufacturing method for biochip 212 in which fibrous substance 217 is formed on first surface 214 of diaphragm part 213 is described.

Figure 12:
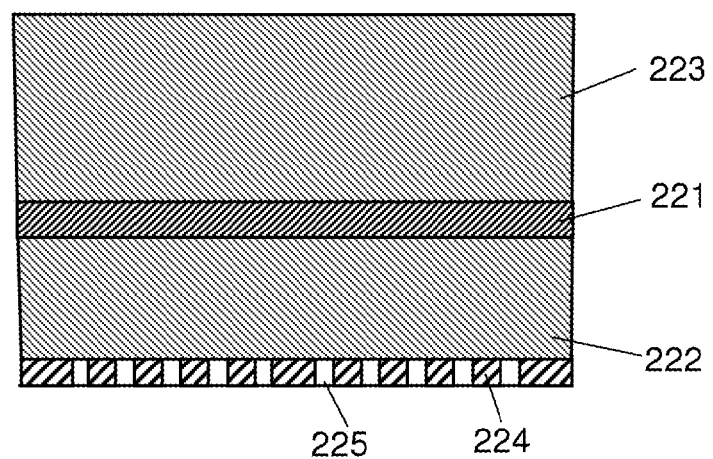
FIG. 12 is a sectional view showing a manufacturing process of the biochip in accordance with the second exemplary embodiment of the present invention.

FIG. 12 is a sectional view showing a manufacturing step of biochip 212 in accordance with the second exemplary embodiment.

Firstly, as a base material for producing biochip 212, a SOI substrate having a three-layered structure of silicon layer 222—silicon dioxide layer 221—silicon layer 223 is prepared. Herein, silicon layer 222 includes silicon (100).

Then, first resist mask 224 is formed on a surface of silicon layer 222 (lower surface in FIG. 12). A plurality of mask holes 225 having substantially the same shape as the shape of the cross-section of a plurality of desired through-holes is patterned to first resist mask 224.

Figure 13:
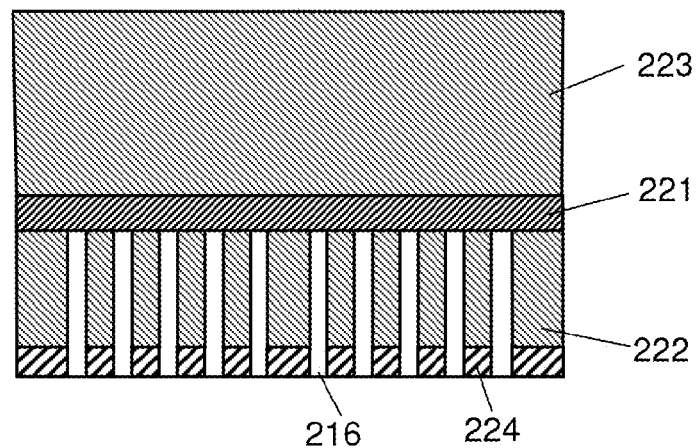
FIG. 13 is a sectional view showing a manufacturing process of the biochip in accordance with the second exemplary embodiment of the present invention.

Next, as shown in FIG. 13, silicon layer 222 is etched from a mask hole 225 side to form through-hole 116. Etching is carried out as in the first exemplary embodiment, so that the etching reaches the surface of silicon dioxide layer 221. Entering of the etching in the depth direction stops at the surface of silicon dioxide layer 221.

Figure 14:
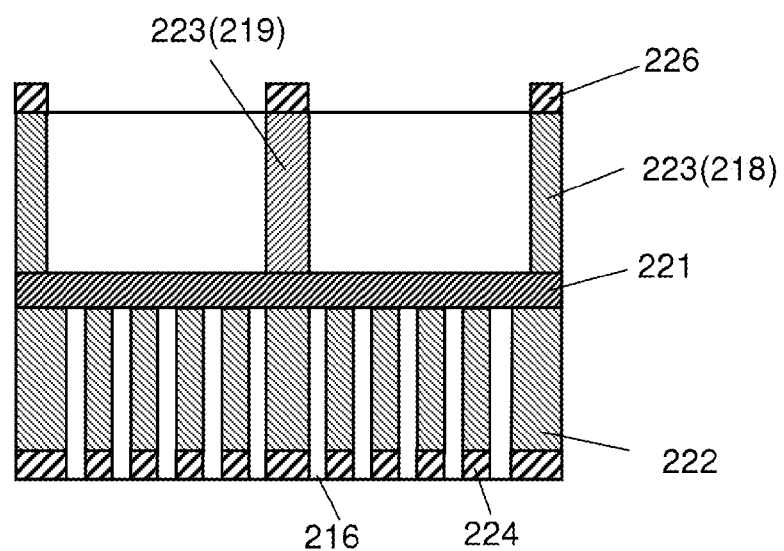
FIG. 14 is a sectional view showing a manufacturing process of the biochip in accordance with the second exemplary embodiment of the present invention.

Next, as shown in FIG. 14, second resist mask 226 is formed on a surface (the upper surface in FIG. 14) of silicon layer 223. Then, silicon layer 223 is etched in the same etching conditions as those when silicon layer 222 is etched. Thus, wall part 218 and reinforcing part 219 are formed. The proceeding of this etching in the depth direction also stops at the surface of silicon dioxide layer 221.

Figure 15:
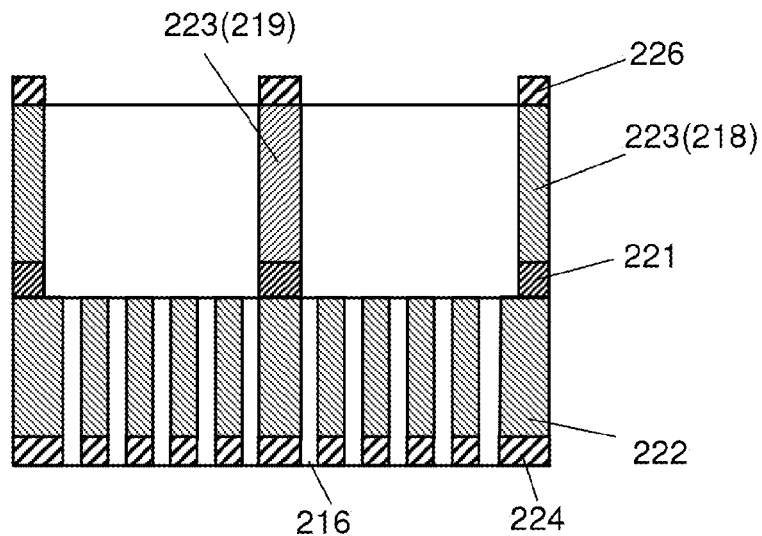
FIG. 15 is a sectional view showing a manufacturing process of the biochip in accordance with the second exemplary embodiment of the present invention.

Next, as shown in FIG. 15, silicon dioxide layer 221 is etched from a surface (upper surface in FIG. 15) of silicon layer 223. As the etching gas to be used for this dry etching, for example, a mixture gas of $CHF_3$ and Ar is used. In the mixture gas of $CHF_3$ and Ar, a plasma-excited Ar gas serves as an etching gas having high straightness. By using a large amount of component, for example, an Ar ion, for carrying out sputtering, the etching proceeds straight from the inside of wall part 218, so that only silicon dioxide layer 221 as an insulating body can be etched.

Other etching gases include $CF_4$, He, and $SF_6$.

Next, a method for forming fibrous substance 217 from a portion provided with catalyst layer 227 is described.

Figure 16:
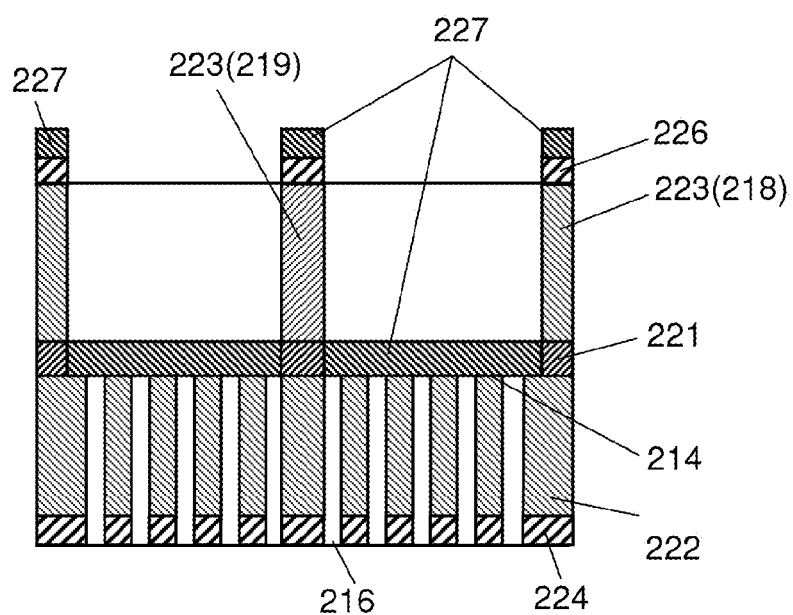
FIG. 16 is a sectional view showing a manufacturing process of the biochip in accordance with the second exemplary embodiment of the present invention.

As shown in FIG. 16, catalyst layer 227 is formed on first surface 214 from the upper side of through-hole 216 (the upper surface in FIG. 16). At this time, in a region in which second resist mask 226 is formed, catalyst layer 227 is formed on the upper surface of second resist mask 226. A thickness of catalyst layer 227 is generally 100 nm or less.

For catalyst layer 227, for example, metal such as Fe, Co, Ni or Au in addition to Pt can be used, and types of metal are not particularly limited.

Note here that examples of a method for forming catalyst layer 227 include a CVD method, a sputtering method, a CSD method, an ALD (Atomic Layer Deposition) method, a VSD (Vaporized Substrate Deposition) method, a VLS (Vapor Liquid Solid) method, and the like. Furthermore, catalyst layer 227 may be provided in a state in which it is dispersed in the other material such as an organic matter.

When the VSD method or the VLS method is used, in a state in which fibrous substance 217 is formed, catalyst material is provided mainly at the tip of fibrous substance 217 or on the surface of the base material that is directly bonded to fibrous substance 217. Existence of the catalyst material can be noticed by observing the tip or the surface using an electron microscope such as a TEM.

Figure 17:
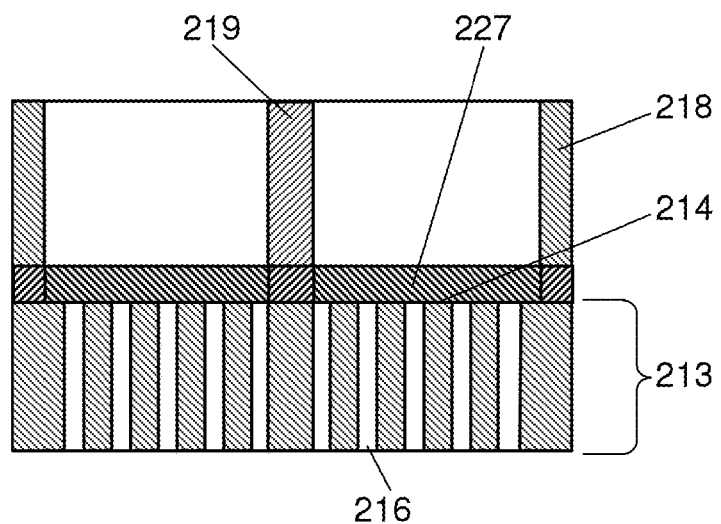
FIG. 17 is a sectional view showing a manufacturing process of the biochip in accordance with the second exemplary embodiment of the present invention.

Next, second resist mask 226 is washed and peeled off. At this time, catalyst layer 227 formed on the upper surface of second resist mask 226 is simultaneously removed. Thus, as shown in FIG. 17, catalyst layer 227 is selectively formed only on first surface 214 of diaphragm part 213. At this time, first resist mask 224 previously formed is simultaneously washed and peeled off.

Figure 18:
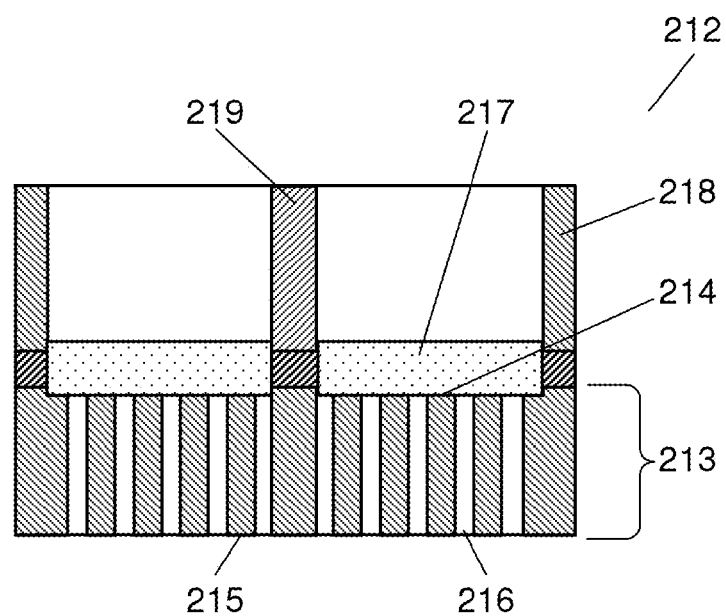
FIG. 18 is a sectional view showing a manufacturing process of the biochip in accordance with the second exemplary embodiment of the present invention.

Next, fibrous substance 217 is formed by using the VSD method as shown in FIG. 18. At this time, fibrous substance 217 is selectively formed on a desired position in which catalyst layer 227 is formed. The position in which catalyst layer 227 is formed can be arbitrarily changed depending upon positions in which first resist mask 224, second resist mask 226 and the other resist masks are formed. Fibrous substance 217 can be formed in only positions provided with a catalyst, for example, only through-hole 216, only first surface 214 of diaphragm part 213, only second surface 215 of diaphragm part 213, only both surfaces of diaphragm part 213, and the like. That is to say, fibrous substance 217 can be formed on arbitrary positions.

A thickness of fibrous substance 217 is generally 1 μm or more and 500 μm or less. The thickness of fibrous substance 217 can be controlled depending upon the conditions.

When fibrous substance 217 made of silicon dioxide is formed by the VSD method, first raw material is an oxidizing gas such as oxygen and ozone, and second raw material is material including silicon as a main component.

When a biochip is heat-treated at a high temperature of 1000° C. or higher and 1500° C. or lower and at a low oxygen concentration, silicon monoxide evaporates from silicon layer 222 and/or silicon layer 223, and is attached again and aggregated on the surface of the biochip and silicon oxide grows. At this time, silicon monoxide spreads over a silicon surface of the silicon layer, but it is attached again selectively to a place on which a catalyst layer is formed, and is bound to oxygen. Thus, fibrous substance 217 including silicon dioxide as a main component grows.

Herein, the low oxygen concentration denotes that an oxygen partial pressure at the time of heat-treatment is low, and it may be a depressurized state in which pressure of the environmental air is lower than the atmospheric pressure, and may be a state in which other gases are substituted for oxygen. Examples of the other gasses include nitrogen, argon, carbon monoxide, or the like. The gases include gases having low oxidizing property unlike oxygen and ozone. Note here that when the oxygen partial pressure is too low, silicon monoxide is not generated. Therefore, the oxygen partial pressure is desirably in the range from $10^{-2}$ Pa to several thousands Pa.

Thereafter, if necessary, an entire surface of biochip 212 may be coated with a hydrophilic film (not shown) by subjecting biochip 212 to thermal oxidation or thermal nitriding.

From the above-mentioned processes, fibrous substance 217 is formed in the arbitrary positions.

A shape of biochip 212 in the top view includes arbitrary shapes such as a square shape, a parallelogram shape, a rectangular shape, a circular shape, and an elliptic shape. For example, when the shape of biochip 212 in the top view is made to be a circular shape, a general glass tube or a tube can be used as mount base 211. Furthermore, biochip 212 is produced from a silicon wafer, it is preferable that biochip 212 is formed into a square shape and a rectangular shape. It is preferable because a large number of biochips 212 can be densely arranged on the silicon wafer, and the number of products can be increased.

(Third Exemplary Embodiment)

Hereinafter, a filter device using a filter chip as a biodevice using a biochip is described as an example with reference to drawings.

FIG. 19 is an enlarged sectional view of a principal part of biochip 312 in accordance with a third exemplary embodiment. This exemplary embodiment is different from the first and second exemplary embodiments in that wall part 318 for holding diaphragm part 313 and reinforcing part 319 are provided at a second surface 315 side of diaphragm part 313 as shown in FIG. 19.

On the upper surface of first surface 314 of diaphragm part 313, a reinforcing part is not formed and only fibrous substance 317 is formed. On the lower surface of second surface 315 of diaphragm part 313, reinforcing part 319 is formed. Consequently, fibrous substance 317 and the reinforcing part do not coexist at a first surface 314 side of biochip 312.

Diaphragm part 313 is etched from a second surface 315 side to form wall part 318 directly bonded to the lower surface of second surface 315, and to form reinforcing part 319 so as to be connected to second surface 315 and wall part 318.

At this time, it is desirable that wall part 318 is formed also on first surface 314 of diaphragm part 313 because diaphragm part 313 becomes stronger.

Thus, when reinforcing part 319 is connected only to second surface 315 without being connected to first surface 314, since the reinforcing part is not formed on first surface 314, fibrous substance 317 can be formed on the entire surface of first surface 314 of diaphragm part 313. Therefore, a contact area between filtration residues and fibrous substance 317 is increased, and thus filtration can be carried out more efficiently. That is to say, material contained in a solution can be filtered through fibrous substance 317 without being influenced by reinforcing part 319.

Furthermore, since reinforcing part 319 is provided at the second surface 315 side of diaphragm part 313, it is possible to suppress displacement of diaphragm part 313 due to a load at the time of filtration. As a result, the strength of diaphragm part 313 can be kept.

Furthermore, when fibrous substance 317 is formed by using, for example, the VSD method, an oxygen gas to be supplied to first surface 314 of diaphragm part 313 can be supplied uniformly to first surface 314 easily. As a result, quality is improved.

Figure 20:
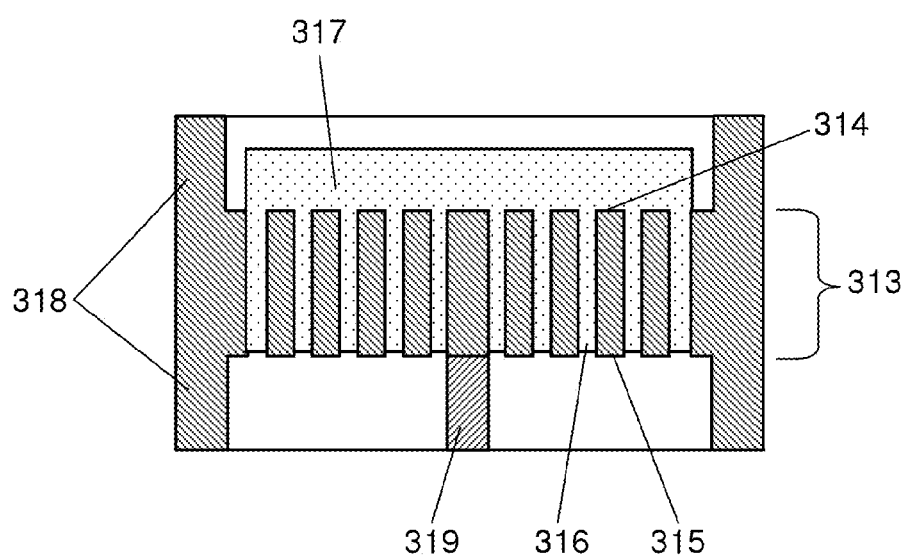
FIG. 20 is an enlarged sectional view of a principal part of a biochip in accordance with the third exemplary embodiment of the present invention.
Figure 21:
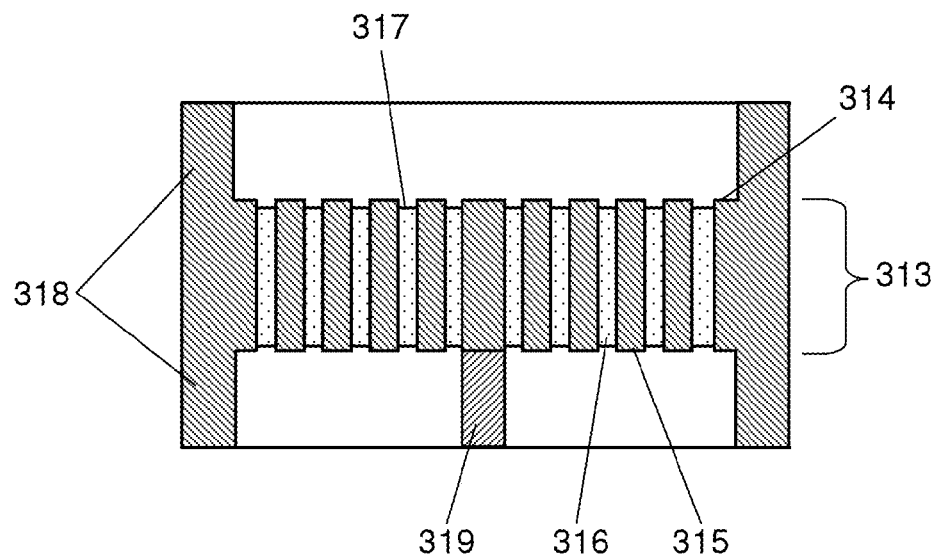
FIG. 21 is an enlarged sectional view of a principal part of a biochip in accordance with the third exemplary embodiment of the present invention.

Fibrous substance 317 may be provided to the inside of through-hole 316 as shown in FIG. 20. Furthermore, fibrous substance 317 is not necessarily brought into contact with first surface 314 or second surface 315, and it may be provided in a flow passage part (inside through-hole 316) through which a solution containing a filtration component passes, as shown in FIG. 21.

In the manufacturing method in accordance with this exemplary embodiment, only by changing a resist mask (not shown) to be formed on second surface 315 of diaphragm part 313, a biochip can be produced by the same method as in the first and second exemplary embodiments.

Figure 23:
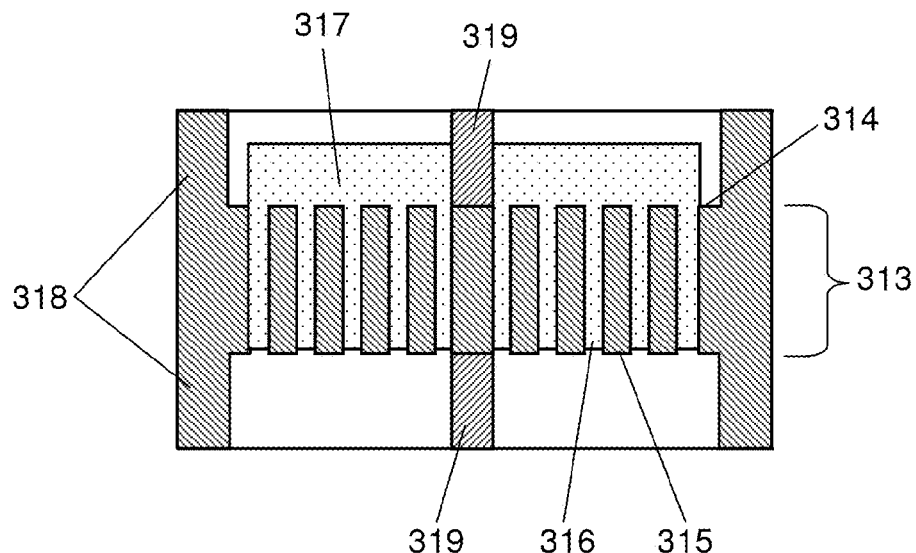
FIG. 23 is an enlarged sectional view of a principal part of a biochip in accordance with the third exemplary embodiment of the present invention.
Figure 24:
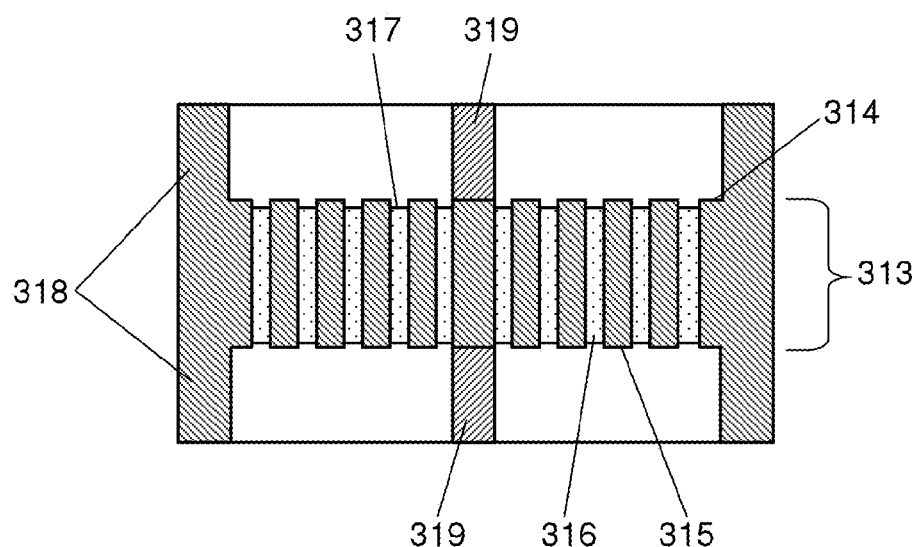
FIG. 24 is an enlarged sectional view of a principal part of a biochip in accordance with the third exemplary embodiment of the present invention.
Figure 25:
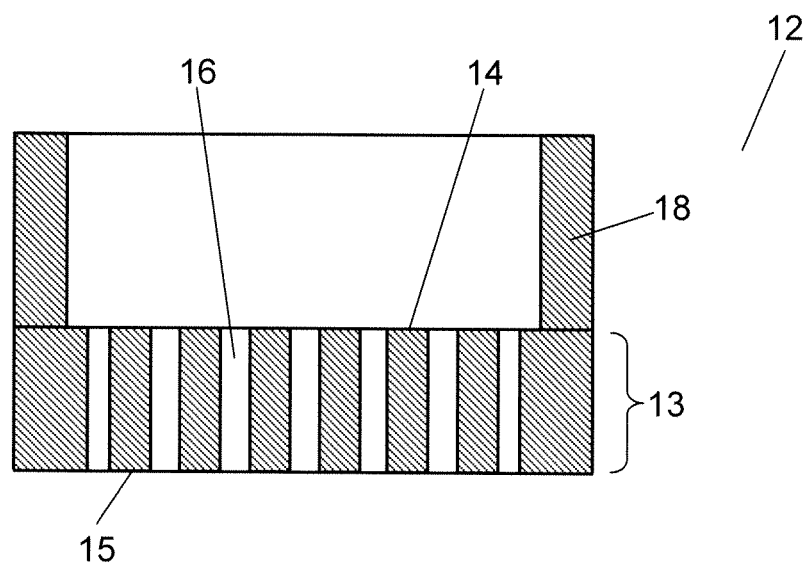
FIG. 25 is a sectional view of a conventional biochip.

Note here that in order to improve the strength of diaphragm part 313, as shown in FIGS. 22, 23, and 24, each of reinforcing parts 319 may be formed on both first surface 314 and second surface 315.

Furthermore, reinforcing parts 319 are formed on first surface 314 and second surface 315 such that the numbers and shapes of reinforcing parts 319 are asymmetrical in the vertical direction. It is preferable that reinforcing parts 319 are dispersed such that a pressure loaded at the time of filtration is dispersed uniformly in the plane of diaphragm part 313.

It is preferable that reinforcing part 319 has a surface having a wave shape or a sawtooth shape and being coated with a hydrophilic film such as an oxide film as in the first and second exemplary embodiments.

Wall part 318 that is brought into contact with first surface 314 and wall 318 that is brought into contact with second surface 315 have thicknesses that are asymmetrical in the vertical direction.

When the biodevice of this exemplary embodiment is used as a filter device, it is useful for various filter devices such as separation filters, sterile filters, and particle filters.

As mentioned above, in the biochip of this exemplary embodiment, by providing a reinforcing part for strongly supporting a diaphragm part, a pressure (force) to the diaphragm part, which is generated when a cell is sucked and brought into contact or at the time of filtration, can be dispersed, and at the same time, displacement with respect to the diaphragm part can be reduced. Therefore, the strength of the diaphragm part can be improved by reducing stress concentration, and damage of a structurally weak diaphragm part can be reduced.

Furthermore, when the biochip of this exemplary embodiment is used as a cell electrophysiological sensor chip, the reinforcing part can be provided without being brought into direct contact with the through-hole. Therefore, the strength of the diaphragm part can be improved without reducing the retention rate of a cell on the through-hole.

Furthermore, when the biochip of this exemplary embodiment is used as a filter chip, the reinforcing part can be provided without being brought into direct contact with the through-holes or the fibrous substance. Therefore, the strength of the diaphragm part can be improved without reducing the filtration efficiency of the through-hole or the fibrous substance. Thus, it becomes easy to change a size (area) of a filter with respect to the amounts of filtrate that is allowed to flow and filtration residues, or to increase a pressure for shortening a filtration time. Furthermore, a function of a filtration filter can be added with high accuracy without loss of performance of fibrous substance due to residues.

INDUSTRIAL APPLICABILITY

As mentioned above, a biochip and a biodevice using the biochip in accordance with the exemplary embodiments can suppress a breakage or displacement of a diaphragm part, and strength can be improved. Therefore, they are useful for medical and biotechnology fields.

REFERENCE MARKS IN THE DRAWINGS 110, 210 biodevice
111, 211 mount base
112, 212, 312 biochip
113, 213, 313 diaphragm part
114, 214, 314 first surface
115, 215, 315 second surface
116, 116a, 116b, 216, 316 through-hole (first through-hole)
118, 218, 318 wall part
119, 219, 319 reinforcing part
119a, 219a first reinforcing part
119b, 219b second reinforcing part
120, 220 hole (second through-hole)
121, 221 silicon dioxide layer
122, 222 silicon layer
123, 223 silicon layer
124, 224 first resist mask
125, 225 mask hole
126, 226 second resist mask
217, 317 fibrous substance
227 catalyst layer

The invention claimed is:

1. A biochip comprising:
a plate-like diaphragm part provided with a through-hole, the plate-like diaphragm part having a first surface and a second surface which is opposite to the first surface, the through-hole penetrating from the first surface to the second surface;
a wall part provided at an outer periphery of the diaphragm part;
a reinforcing part formed in a portion other than the through-hole in the diaphragm part; and
a fibrous substance formed on the first surface of the diaphragm part so as to cover an opening part of the through-hole, the fibrous substance having a plurality of fibers,
wherein the plurality of fibers are entangled with each other, and
the first surface of the plate-like diaphragm part, a surface of the wall part, a surface of the reinforcing part and the fibrous substance are made of silicon oxide.

2. The biochip of claim 1, wherein the reinforcing part contacts the diaphragm part.

3. The biochip of claim 1, wherein the reinforcing part contacts the wall part.

4. The biochip of claim 1, wherein the reinforcing part has a plate-like shape.

5. The biochip of claim 1, wherein the reinforcing part is one of a plurality of reinforcing parts, and the plurality of reinforcing parts is formed in a portion other than the through-hole in the diaphragm part.

6. The biochip of claim 1, wherein the diaphragm part includes a first surface and a second surface opposite to the first surface,
the first surface and the second surface include an opening part of the through-hole, and
the reinforcing part is formed on at least one of the first surface and the second surface.

7. The biochip of claim 1, wherein the diaphragm part includes a first surface and a second surface opposite to the first surface,
the first surface and the second surface include an opening part of the through-hole, and
the wall part is formed on at least one of the first surface and the second surface.

8. The biochip of claim 1, wherein the through-hole is one of a plurality of through-holes, and the plurality of through-holes is formed in the diaphragm part.

9. The biochip of claim 1, wherein the fibrous substance directly contacts the diaphragm part.

10. The biochip of claim 1, wherein the diaphragm part includes a first surface and a second surface opposed to the first surface,
the first surface and the second surface include an opening part of the through-hole, and
the fibrous substance is formed on at least one of the first surface and the second surface.

11. The biochip of claim 1, wherein the fibrous substance separates material whose maximum diameter is larger than a gap in the fibrous substance by filtration.

12. The biochip of claim 1, wherein the fibrous substance separates leukocyte in blood by filtration.

13. The biochip of claim 1, wherein the fibrous substance is formed inside the through-hole.

14. A biodevice comprising:
a mount base provided with a hole; and
a biochip provided inside the hole of the mount base, comprising:
a plate-like diaphragm part provided with a through-hole, the plate-like diaphragm part having a first surface and a second surface which is opposite to the first surface, the through-hole penetrating from the first surface to the second surface;
a wall part provided at an outer periphery of the diaphragm part; and
a reinforcing part formed in a portion other than the through-hole in the diaphragm part; and
a fibrous substance formed on the first surface of the diaphragm part so as to cover an opening part of the through-hole, the fibrous substance having a plurality of fibers,
wherein the plurality of fibers are entangled with each other, and
the first surface of the plate-like diaphragm part, a surface of the wall part, a surface of the reinforcing part and the fibrous substance are made of silicon oxide.

15. The biochip of claim 1, wherein some fibers of the fibrous substance branch into various directions.

16. The biodevice of claim 14, wherein some fibers of the fibrous substance branch into various directions.

* * * * *